United States Patent [19]

Struve

[11] 4,274,403

[45] Jun. 23, 1981

[54] INHALER

[76] Inventor: Roger L. Struve, P.O. Box 12573, New Brighton, Minn. 55112

[21] Appl. No.: 70,733

[22] Filed: Aug. 29, 1979

[51] Int. Cl.³ .............................................. A61M 15/00
[52] U.S. Cl. .................................................. 128/203.15
[58] Field of Search ................... 128/203.15, 266, 265, 128/213 R

[56] References Cited

U.S. PATENT DOCUMENTS

| 2,534,636 | 12/1950 | Stirn | 128/266 X |
| 2,570,774 | 10/1951 | Davis | 128/266 |
| 2,579,280 | 12/1951 | Trumbour et al. | 128/203.15 |
| 2,581,182 | 1/1952 | Fields | 128/203.15 |
| 2,587,215 | 2/1952 | Priestly | 128/266 X |
| 2,590,832 | 3/1952 | Brown | 128/203.15 |
| 2,642,063 | 6/1953 | Brown | 128/203.15 |
| 3,938,516 | 2/1976 | Mathes | 128/266 |
| 4,184,258 | 1/1980 | Barrington et al. | 128/266 X |
| 4,200,099 | 4/1980 | Guenzel et al. | 128/266 |

FOREIGN PATENT DOCUMENTS 628931 10/1978 U.S.S.R. ............................... 128/203.15

Primary Examiner—Henry J. Recla
Attorney, Agent, or Firm—Merchant, Gould, Smith, Edell, Welter & Schmidt

[57] ABSTRACT

An inhaler (2) includes a body (10) having a dispensing head (6) coupled thereto. Body (10) includes a storage chamber (24) for storing a supply of powdered drugs therein and a storage chamber (26) for holding a dessicating agent. A dispensing cylinder (60) contained in a transverse bore (40) in dispensing head (6) is laterally movable from a first transverse position in which a metering chamber (70) is in alignment with the feed hole (38) to a second transverse position in which chamber (70) communicates with the dispensing passageway (48) of nozzle (30). In the first transverse position, metering chamber (70) may be filled and in the second transverse position the drugs contained in chamber (70) may be inhaled through nozzle (30). In addition, a cylindrical insert (76) received around dispensing cylinder (60) seals storage chamber (24) when inhaler (2) is not in use.

15 Claims, 6 Drawing Figures

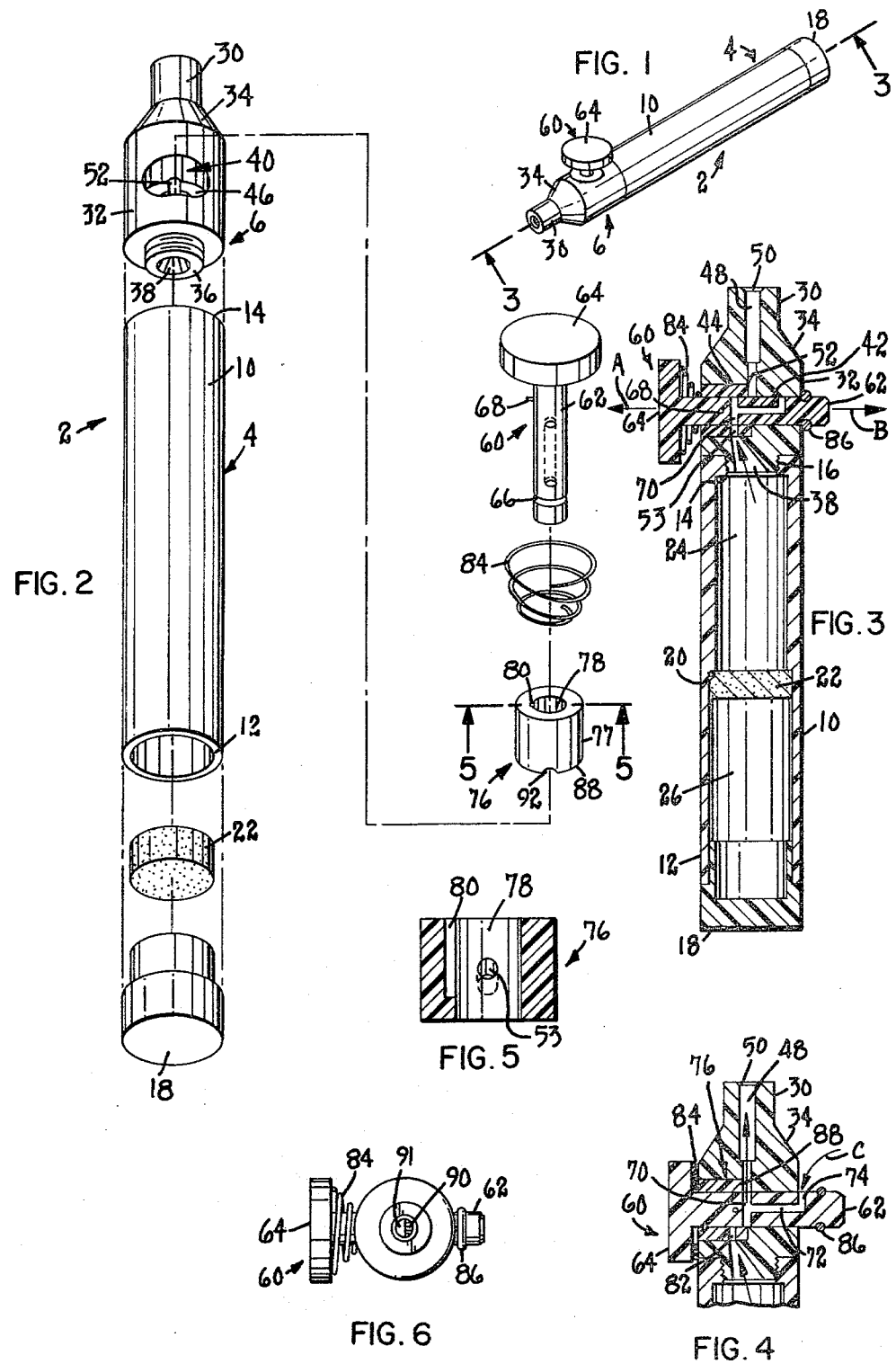

INHALER

TECHNICAL FIELD

This invention relates generally to devices for administering medication in the form of powdered drugs. More particularly, this invention relates to an inhaler which administers the medication nasally upon inhalation by the user.

DESCRIPTION OF THE PRIOR ART

Various medicines or drugs are desirably administered nasally, i.e. through the nose. This is sometimes done because the user being treated has a nasal disease or abnormality for which the medication is particularly effective. Sometimes, it is simply done because nasal inhalation is a convenient way to administer a particular drug. Inhalation of any medication will effect not only the nasal passages but the throat and lungs as well.

Various devices are known which are used for the inhalation of a drug in a powdered or particulate form. These devices generally include a body which holds a suitable supply of the powdered drug. The user inserts the device into his nose, usually by inserting a nozzle into one of the nasal passages, and then inhales. The device is usually constructed so that the air flow which is drawn into the nose first passes through the body of the device to pick up and entrain a small amount of the powdered drug. This drug then enters the nasal passage.

While devices such as those noted above are effective in administering powdered drugs, they have certain disadvantages. For one thing, many drugs, at least in their powdered form, are highly hygroscopic. Many of the known inhalers have no way of storing the powdered drug in an air-tight manner or for removing moisture from the stored drugs. Thus, the drugs which are stored in such an inhaler may become contaminated with water. Such water contaminated drugs will often be unsuitable for their intended use or will clog up various parts of the inhaler when inhalation is attempted.

Another problem with known inhalers is that many do not have any provision for metering the amount of medication which is drawn up into the nasal passage. This amount is often proportionate to the strength of the inhalation by the user. When the amount of medication which is being inhaled is critical or must be precisely measured, many of the known inhalers may have little utility. U.S. Pat. No. 2,587,215 discloses an inhaler which dispenses a measured amount of medication during each use. However, the inhaler disclosed in this patent does not have any way of positively sealing off the drug chamber when not in use. Thus, moisture contamination of the drugs still constitutes a problem. In addition, this device does not disclose any type of means for removing moisture which has already entered the drugs.

SUMMARY OF THE INVENTION

One aspect of the present invention is the provision of an inhaler which is simple and relatively inexpensive to produce. In addition, another aspect of this invention is to provide an inhaler for dispensing a measured amount of a powdered drug into the user's nasal passages during each inhalation operation.

The inhaler according to this invention is designed for administering a powdered drug nasally and comprises storage means for storing a quantity of the drug. The storage means includes a feed hole through which the powdered drug may be removed and a means for removing moisture from the stored drug. In addition, a dispensing means is operatively connected to the feed hole for dispensing the powdered drug nasally. The dispensing means comprises a nozzle means which is suited to be received in one of the nasal passages of the user. It also includes a means for measuring and transferring a pre-determined charge of the powdered drug from the feed hole of the storage means to the nozzle means. The pre-determined charge of the drug has a volume less than the stored quantity of the powdered drug. The dispensing means further includes vent means for communicating with ambient air and the nozzle means for allowing air to be drawn into the nozzle means for carrying the charge of the drug upwardly into the nasal passage of the user. Finally, the dispensing means includes a means for positively sealing the feed hole whenever the inhaler is not in use for storing the powdered drug therein in an air tight manner.

BRIEF DESCRIPTION OF THE DRAWINGS

This invention will be described in more detail hereafter in the Detailed Description, when taken in conjunction with the following drawings, in which like reference numerals refer to like elements throughout.

FIG. 1 is a perspective view of an inhaler according to the present invention;

FIG. 2 is a perspective view of the inhaler shown in FIG. 1 with the components thereof being shown in an exploded form to illustrate the manner in which they interfit together;

FIG. 3 is a cross-sectional view of the inhaler shown in FIG. 1 taken along lines 3—3 of FIG. 1, particularly illustrating the dispensing cylinder in the first transverse position thereof in which the metering chamber communicates with the feed hole leading to the drug storage chamber;

FIG. 4 is a partial enlarged cross-sectional view of the dispensing head similar to the representation of the dispensing head as shown in FIG. 3, particularly illustrating the dispensing cylinder in a second transverse position thereof in which the metering chamber is in communication with the vertical passageway in the nozzle means and with the air vent being exposed to ambient air;

FIG. 5 is a cross-sectional view of a cylindrical insert which surrounds a portion of the dispensing cylinder; and FIG. 6 is a top elevational view of the inhaler shown in FIG. 1, particularly illustrating the insert in a second radial position in which the metering chamber is not aligned with the feed hole leading to the drug storage chamber.

DETAILED DESCRIPTION

Referring first to FIGS. 1 and 2, an inhaler according to the present invention is generally illustrated as 2. Inhaler 2 is particularly suited for administering a powdered medication or drug nasally, i.e. into one of the nasal passages of the user. The type of drug being administered is not important to this invention and may comprise any drug which is desirably administered to the nasal passages. For example, penicillin is one drug which is sometimes administered in this manner. The dispending action of inhaler 2 is obtained solely from the inhalation of the user. No powdered dispensing means, such as a motor driven pump, is required.

Inhaler 2 comprises a storage means, generally indicated as 4, for storing a suitable quantity of the powdered drug therein. In addition, inhaler 2 includes a dispensing means in the form of a dispensing head 6 releasably secured to storage means 4. Dispensing head 6 measures and dispenses a pre-determined charge of the powdered drug contained in storage means 4 into one of the nasal passages of the user. Preferably, this pre-determined charge of the drug has a volume which is significantly less than the quantity of the drug stored in storage means 4 so that inhaler 2 is a multi-use instrument. Whenever inhaler 2 is not being used for administering the powdered drug, it serves as a convenient tool for storing the drug.

THE STORAGE MEANS

Referring now to FIGS. 2 and 3, storage means 4 comprises a longitudinally elongated body 10. Body 10 is a hollow cylinder having an open lower end 12 and an open upper end 14. Upper end 14 of body 10 is threaded as indicated at 16 for releasably receiving dispensing head 6. Preferably, open lower end 12 of body 10 is normally closed by a removable cap or cover 18. Cap 18 is received in a force-fit in lower end 12 of body 10.

Body 10 does not have a uniform wall thickness throughout its entire length. Rather, the wall thickness of body 10 reduces at a point intermediate the ends 12 and 14 to effectively define an annular shoulder or lip 20 on the inner-diameter of body 10. A circular, moisture-porous plug 22 is fixedly contained inside body 10 located against the shoulder 20. Plug 22 is glued or otherwise fixedly secured to body 10 in the position illustrated in FIG. 3. Any suitable materials could be used for plug 22 as long as such materials are porous to the passage of moisture. Plug 22 effectively divides body 10 into two elongated storage chambers generally referred to as 24 and 26. While shoulder 20 is preferably formed in the manner described, any other conventional means for forming the shoulder could be used, e.g. by an annular sealing ring or the like fixedly secured to the inner diameter of a cylinder having a uniform wall thickness.

Storage chamber 24 preferably receives therein a relatively large quantity of the powdered drug which is to be administered by inhaler 2. Storage chamber 26 in turn preferably receives a dessicating agent therein of any known type. This dessicating agent is effective through porous plug 22 in removing any moisture which is entrained in the powdered drug contained in storage chamber 24. As such, the dessicating agent serves to keep the powdered drug dry. This is important for any drugs that are highly hygroscopic. Some drugs when contaminated with water would be ruined for their intended physiological use and/or would clog up various of the parts of dispensing head 6. The use of a dessicating agent in storage chamber 26 avoids these problems. The dessicating agent can be removed and replaced in storage chamber 26 since end cap 18 is removable.

THE DISPENSING HEAD

Dispensing head 6 includes a circularly shaped, longitudinally elongated nozzle 30. Nozzle 30 has a diameter sufficiently small such that it can be easily received inside the nasal passages of a typical user. A cylindrical body section or portion 32, having an outside diameter to match the outside diameter of body 10 is located beneath nozzle 30. Preferably, nozzle 30 and body portion 32 are integrally connected together by means of a tapering conical section 34. In addition, body section 32 includes an outwardly extending exteriorly threaded nipple 36. Nipple 36 is threadedly received in the threads 16 on body 10 to releasably join dispensing head 6 to body 10. Nipple 36 includes a vertically extending feed hole 38. The purpose of feed hole 38 is simply to connect dispensing head 6 to the supply of the powdered drug contained in storage chamber 24.

Body section 32 of dispensing head 6 has a transverse bore, generally identified as 40, extending all the way therethrough. Bore 40 includes a first section 42 and a side by side second section 44. Section 44 has a diameter which is greater than the diameter of section 42. Both of the sections 42 and 44 open at one end on one of the sides of body section 32. Bore sections 42 and 44 come together at their other ends along a junction plane defined generally by a vertical annular ring or face 46. (See FIG. 2)

Nozzle 30 includes a vertically extending dispensing passageway 48. Dispensing passageway 48 includes an open upper end 50 in the tip of nozzle 30 and a lower end 52 which enters transverse bore 40 along the vertical face 46 thereof. In addition, feed hole 38 enters transverse bore 40 in the bore section 44 as indicated at 53. Thus, dispensing passageway 48 and feed hole 52 are transversely offset along the length of transverse bore 40. In order to establish communication between feed hole 38 and dispensing passageway 48 for the purpose of dispensing a portion of the powdered drug contained in storage chamber 44, a dispensing cylinder generally indicated as 60 is used.

Dispensing cylinder 60 includes an elongated cylindrical body portion 62. An enlarged head 64 is located at one end of body portion 62. An annular groove 66 is formed in the cylindrical body portion 62 adjacent the other end thereof. A pin or lug 68 extends radially outwardly from body portion 62 and is located adjacent the enlarged head 64. Body portion 62 is sufficiently long such that it extends all the way through transverse bore 40 as shown in FIG. 3. In this position, enlarged head 64 is located on one side of the body portion 32 of dispensing head 6 and the annular groove 66 is located on the other side of the body portion 32.

Referring now to FIG. 4, dispensing cylinder 60 includes a metering chamber generally indicated as 70. Metering chamber 70 extends vertically all the way through body portion 62 of cylinder 60. A horizontally extending bore 72 connects metering chamber 70 with an air vent 74. Air vent 74 and metering chamber 70 are transversely offset along the length of body portion 62.

A cylindrical insert 76 is received in the enlarged bore portion 44. Cylindrical insert 76 has a circular bore 78 through which body portion 62 slidably extends for movement in the direction of arrows A and b. The inside diameter of bore 78 has a transversely extending slot 80. (See FIG. 5) Slot 80 is designed to receive pin 68 therein. This construction also allows the cylindrical body portion 62 to be slid transversely through bore 78, but couples dispensing cylinder 60 and insert 76 together for conjoint rotation. A vertically extending bore 82 is aligned with metering chamber 70 whenever cylinder 60 is in the position shown in FIG. 3. Insert 76 forms a means for sealing storage chamber 24 in a manner which will be described hereafter.

Referring to FIGS. 3 and 4, dispensing cylinder 60 normally has cylindrical body portion 62 extending through both the insert 76 which is received in the enlarged bore section 44 and through the smaller bore section 42. A spring 84 extends between the enlarged head 64 and one side of the body portion 32 of dispensing head 6. Spring 84 normally forces the dispensing cylinder in the direction indicated by the arrow A. Dispensing cylinder 60 is prevented from sliding all the way out of transverse bore 40 by means of a rubber O-ring 86 received in annular groove 66. O-ring 86 forms an abutment means which engages the other side of body portion 32 to limit movement of the dispensing cylinder in the direction of arrow A.

Referring to FIGS. 3 and 4, spring 84 forces dispensing cylinder 60 into a first transverse position generally indicated in FIG. 3. In this position, metering chamber 70 is in communication with feed hole 38 and thus with storage chamber 24. If, however, dispensing cylinder 60 is depressed against the force of spring 84 to slide cylinder 60 in the direction of arrow B, then cylinder 60 moves into a second transverse position shown in FIG. 4. In this position, metering chamber 70 has been shifted into alignment with dispensing passageway 48 and no longer communicates with feed hole 38. In addition, in this position, air vent 74 is now located outside of body portion 32. Ambient air is thus free to flow into air vent 74 and into metering chamber 70 as illustrated by the arrows C.

Both the cylindrical insert 76 and dispensing cylinder 60 are rotatably received in the bore sections 42 and 44 which comprise transverse bore 40. Normally, they occupy a first radial position as shown in FIG. 3 in which the bore 82 and metering chamber 70 are aligned with feed hole 38. If, however, dispensing cylinder 60 is rotated in a clockwise or counterclockwise direction 90°, the bore 82 will be moved out of alignment with feed hole 38 since insert 76 is coupled to cylindrical body portion 62 for rotation therewith. Thus, these components may be rotated to a second radial position in which the smooth exterior surface 77 of insert 76 covers feed hole 38 for the purpose of sealing feed hole 38 and thus storage member 24. Insert 76 thus forms a means for sealing storage chamber 24 in an air tight manner.

Referring to FIG. 3, when cylindrical insert 76 is received in bore portion 44, an inner face 88 of insert 76 abuts against the vertical face 46 which marks the junction between the bore portions 42 and 44. Thus, the face 88 of insert 76 protrudes half way into the width of dispensing passageway 48. Face 88 appears as a line 90 when one looks down through the open upper end 50 of dispensing passageway 48. Insert 76 also includes a semi-circular cut-out 92 located immediately adjacent face 88. Cut-out 92 is shaped to have a curvature matching that of dispensing passageway 48. In addition, cut-out 92 is located on insert 76 at a particular position such that it will mate with passageway 48 when bore 82 is in alignment with feed hole 38. At all other rotated positions of insert 76, cut-out 92 does not mate with passageway 48. Instead, one sees the half moon representation 91, as shown in FIG. 6, formed by face 88 of insert 76 when viewed through passageway 48. Thus, cut-out 92 serves as a visual means for indicating when metering chamber 70 is in alignment with feed hole 38. All that is required is that the dispensing cylinder 60 be rotated until the half moon shown in FIG. 6 disappears and a complete circle is seen through passageway 48.

USE OF THE INHALER

In using inhaler 2, storage chamber 24 is first filled with a suitable supply or quantity of the powdered drug. Dispensing head 6 is then releasably coupled to body 10. When dispensing cylinder 60 is in its first transverse position of FIG. 3, metering chamber 70 communicates through feed hole 38 with storage chamber 24. If inhaler 2 is then inverted so that dispensing head 6 is below body 10, the powdered drug contained in storage chamber 24 will fall downwardly through feed hole 38 until metering chamber 70 is filled. With inhaler 2 kept in the inverted position, dispensing cylinder 60 is then manually depressed by the user pushing inwardly on enlarged head 64 with his thumb or the like. Metering chamber 70 will then be shifted out of alignment with feed hole 38 and will effectively have measured a predetermined charge of the drug which is equal to the volume of metering chamber 70.

After dispensing cylinder 60 is depressed, inhaler 2 may be placed right side up. While keeping dispensing cylinder 60 depressed, nozzle 30 is then placed into one of the user's nasal passages. With dispensing cylinder 60 still depressed, the user then inhales. The air flow represented by the arrow C will flow in through the now exposed air vent 74 and into metering chamber 70. This air flow will pick up and entrain the powdered drug contained in chamber 70 and carry the drug upwardly through dispensing passageway 48 into the user's nostril. A precisely measured charge of drug has thus been administered nasally by means of this operation. This cycle of steps may be repeated when subsequent charges of drugs are to be administered.

When the user is through administering the drug, dispensing cylinder 60 is then rotated out of its radial position as shown in FIG. 3. Rotation occurs until the half moon representation 91 is seen again in FIG. 6. This indicates that the solid exterior surface 77 of insert 76 has moved over feed hole 38. Thus, the powdered drugs which are still stored in storage chamber 24 will be maintained in an air-tight manner where moisture and other contaminants cannot reach them.

Inhaler 2 according to this invention has many advantages. For one thing, it combines in the same structure means for storing the powdered drugs in an air-tight manner, means for removing moisture from the stored drugs, and means for measuring and dispensing a predetermined charge of the powdered drug. As such, it combines a number of features which are found only individually in prior art inhalers. In addition, the structure of dispensing head 6 is particularly efficient. For example, the dispensing cyliner 60 also includes the means for establishing the air flow through the metering chamber 70. Thus, dispensing head 6 minimizes the number of parts required and as such is inexpensive to produce. It also relatively compact making inhaler 2 easy to carry or store.

Insert 76 is preferred as the means for sealing storage chamber 24 because it is relatively easy to manufacture and install. Insert 76 could be replaced by a rubber sealing plug or the like located on the exterior of cylindrical body portions 62 offset 90° from metering chamber 70. Thus, when dispensing cylinder 60 is rotated 90°, the rubber sealing plug will be superimposed over feed hole 38 to seal off storage chamber 24. However, it is relatively difficult to place such a small rubber plug onto the exterior surface of dispensing cylinder 60. In addition, the presence of such a plug hinders rotation of dispensing cylinder 60 and tends to wear in the bore in which the dispensing cylinder is received. The presence of such a plug also prevents a tight fit for dispensing cylinder 60 in the bore. Thus, insert 76 which does not have these disadvantages, is preferred.

The components of inhaler 2 may be made of any suitable materials. Preferably, relatively rigid plastic or thermoplastic materials are preferred.

Various modifications of this invention will be apparent to those skilled in the art. Thus, the scope of this invention is to be limited only by the appended claims.

What is claimed is:

1. An inhaler for administering a powdered drug nasally, which comprises:
    (a) storage means for containing a quantity of the powdered drug, wherein the storage means includes:
        (i) an elongate body divided into first and second chambers by a moisture permeable plug, said first chamber being suited for receiving a powdered drug and said second chamber being suited for receiving a dessicating agent which withdraws moisture from the powdered drug, wherein said second chamber is closed to the external environment and opens only into said first chamber, through said moisture permeable plug;
        (ii) a feed hole opening into said first chamber through which the powdered drug may be removed therefrom; and
    (b) dispensing means operatively connected to the feed hole of the storage means for dispensing the powdered drug nasally, wherein the dispensing means comprises:
        (i) nozzle means suited to be received in one of the nasal passages of the user;
        (ii) means for measuring and transferring a predetermined charge of the powdered drug from the storage means to the nozzle means, wherein the pre-determined charge has a volume less than the stored quantity of the powdered drug originally contained in the storage means;
        (iii) vent means for allowing ambient air to be drawn into the nozzle means for carrying the powdered charge therein upwardly into the nasal passage of the user upon inhalation of the user; and
        (iv) means for positively sealing the feed hole of the storage means from the external environment whenever the inhaler is not in use so that the powdered drug contained therein is stored in an air-tight manner.

2. An inhaler as recited in claim 1, wherein the dispensing means is releasably coupled to the storage means.

3. An inhaler as recited in claim 1, in which the dispensing means comprises a dispensing head coupled to the storage means, wherein the dispensing head comprises:
    (a) a nozzle shaped to be received in the nasal passage of the user, wherein the nozzle includes a dispensing passageway;
    (b) a body portion adjacent the nozzle and having a transverse bore therein which operatively connects the dispensing passageway in the nozzle with the feed hole in the storage means, wherein the feed hole and the dispensing passageway are transversely offset relative to one another at the points where they enter the transverse bore; and
    (c) a dispensing cylinder having a metering chamber which may be selectively aligned with either the feed hole or the dispensing passageway, wherein the dispensing cylinder is slidably received in the transverse bore for movement between a first transverse position in which the metering chamber is aligned with the feed hole and a second transverse position in which the metering chamber is aligned with the dispensing passageway, wherein the metering chamber in its first position can be filled with the pre-measured charge of the powdered drug when the inhaler is manipulated and in the second position places the pre-determined charge of the powdered drug into the dispensing passageway for inhalation by the user.

4. An inhaler as recited in claim 3, wherein the vent means is formed as part of the dispensing cylinder and is operative only in the second position of the cylinder.

5. An inhaler as recited in claim 4, wherein the vent means comprises an air vent located in the dispensing cylinder in communication with the metering chamber, wherein the air vent is located adjacent one end of the dispensing cylinder such that it is closed by the transverse bore in the first position of the dispensing cylinder and is located outside of the body portion of the dispensing head in the second position of the dispensing cylinder so that the inhalating air flow passes in through the air vent, through the metering chamber, and into the dispensing passageway.passageway.

6. An inhaler as recited in claim 3, wherein the dispensing cylinder is normally biased into its first position.

7. An inhaler as recited in claim 6, wherein the dispensing cylinder is sufficiently long such that its opposed ends are located outside of the body portion on opposite sides thereof, wherein one end of the cylinder has an enlarged head and the other end of the cylinder has abutment means for engaging the body portion, and further including a spring extending between the body portion and the enlarged head to bias the cylinder into its first position defined as the position in which the abutment means engages the body portion.

8. An inhaler as recited in claim 3, wherein the sealing means comprises a cylindrical insert received around the dispensing cylinder at the location of the metering chamber, wherein the insert includes a bore which is aligned with the metering chamber in the first transverse position of the dispensing cylinder, and wherein both the insert and the dispensing cylinder are rotatably received in the dispensing head for conjoint rotation between a first radial position in which the insert bore and metering chamber are in communication with the feed hole and a second radial position in which the insert itself blocks the feed hole to store the powdered drug in the storage means in an air-tight manner.

9. An inhaler for administering a powdered drug nasally, which comprises:
    (a) storage means for containing a quantity of the powdered drug, wherein the storage means includes:
        (i) a feed hole through which the powdered drug may be removed from the storage means; and
        (ii) means for removing moisture from the stored drug; and
    (b) dispensing means operatively connected to the feed hole of the storage means for dispensing the powdered drug nasally, wherein the dispensing means comprises:

(i) a nozzle shaped to be received in the nasal passage of the user, wherein the nozzle includes a dispensing passageway;

(ii) a body portion adjacent the nozzle and having a transverse bore therein which operatively connects the dispensing passageway in the nozzle with a feed hole in the storage means, wherein the feed hole and the dispensing passageway are transversely offset relative to one another at the points where they enter the transverse bore;

(iii) a dispensing cylinder having a metering chamber which may be selectively aligned with either the feed hole or the dispensing passageway, wherein the dispensing cylinder is slidably received in the transverse bore for movement between a first transverse position in which the metering chamber is aligned with the feed hole and a second transverse position in which the metering chamber is aligned with the dispensing passageway; wherein the metering chamber in its first position can be filled with a pre-measured charge of the powdered drug when the inhaler is manipulated and in the second position places the pre-determined charge of the powdered drug into the dispensing passageway for inhalation by the user;

(iv) vent means for allowing ambient air to be drawn into the nozzle means for carrying the powdered charge therein upwardly into the nasal passage of the user upon inhalation of the user; and (v) means for sealing the feed hole of the storage means whenever the inhaler is not in use so that the powdered drug contained therein is stored in an air-tight manner, comprising: a cylindrical insert received around the dispensing cylinder at the location of the metering chamber, wherein the insert includes a bore which is aligned with the metering chamber in the first transverse position of the dispensing cylinder, and wherein both the insert and the dispensing cylinder are rotatably received in the dispensing head for conjoint rotation about a first radial position in which the insert bore and metering chamber are in communication with the feed hole and a second radial position in which the insert itself blocks the feed hole to store the powdered drug in the storage means in an air-tight manner.

10. An inhaler as recited in claim 9, in which the insert includes means for visually indicating when the insert is in its first radial position with the insert bore in alignment with the feed hole to enable the metering chamber to be filled with the pre-determined charge.

11. An inhaler as recited in claim 10, in which the visual indicating means comprises one end of the insert which is positioned to partially lie in the dispensing passageway of the nozzle, and wherein the one end of the insert includes a semi-circular cut-out portion which is shaped to match the configuration of the dispensing passageway when superimposed therewith, wherein the cut-out portion is located relative to the insert bore such that the cut-out portion is superimposed with the dispensing passageway only in the first radial portion of the insert and dispensing cylinder, whereby the user looking through the dispensing passageway will know that the insert bore is in alignment with the feed hole when the cut-out portion is superimposed with the dispensing passageway.

12. An inhaler as recited in claim 9, wherein the insert is separate from the dispensing chamber and is rotatably coupled thereto by a pin and slot interconnection.

13. An inhaler for administering a powdered drug nasally, which comprises:

(a) storage means for containing a quantity of the drug therein, said storage means including a feed hole through which the powdered drug may be received from the storage means:

(b) a dispensing head operatively coupled to the storage means for dispensing the powdered drug more nasally, wherein the dispensing head comprises:

(i) a nozzle shaped to be received in the nasal passage of the user, wherein the nozzle includes a dispensing passageway;

(ii) a body portion adjacent the nozzle and having a transverse bore therein which operatively connects the dispensing passageway in the nozzle with the feed hole leading to the drug storage means, wherein the feed hole and the dispensing passageway are transversely offset relative to one another at the points where they enter the transverse bore;

(iii) a dispensing cylinder having a metering chamber which may be selectively aligned with either the feed hole or the dispensing passageway, wherein the dispensing cylinder is slidably received in the transverse bore for movement between a first transverse position in which the metering chamber is aligned with the feed hole and a second transverse position in which the metering chamber is aligned with the dispensing passageway, wherein the metering chamber in its first position can be filled with a charge of the powdered drug when the inhaler is manipulated and in the second position places the charge of the powdered drug into the dispensing passageway for inhalation by the user; and (iv) vent means formed as part of the dispensing cylinder for venting said metering chamber to atmosphere only in the second position of the cylinder.

14. An inhaler for administering a powdered drug nasally, which comprises:

(a) storage means for containing a quantity of the drug therein, said storage means including a feed hole through which the powdered drug may be removed from the storage means;

(b) a dispensing head operatively coupled to the storage means for dispensing the powdered drug more nasally, wherein the dispensing head comprises:

(i) a nozzle shaped to be received in the nasal passage of the user, wherein the nozzle includes a dispensing passageway;

(ii) a body portion adjacent the nozzle and having a transverse bore therein which operatively connects the dispensing passageway in the nozzle with the feed hole leading to the storage means, wherein the feed hole and the dispensing passageway are transversely offset relative to one another at the points where they enter the transverse bore;

(iii) a dispensing cylinder having a metering chamber which may be selectively aligned with either the feed hole or the dispensing passageway, wherein the dispensing cylinder is slidably received in the transverse bore for movement between a first transverse position in which the metering chamber is aligned with the feed hole and a second transverse position in which the metering chamber is aligned with the dispensing passageway, wherein the metering chamber in its first position can be filled with a charge of the powdered drug when the inhaler is manipulated and in the second position places the charge of the powdered drug into the dispensing passageway for inhalation by the user; and (iv) a sealing means which comprises a cylindrical insert received around the dispensing cylinder at the location of the metering chamber, wherein the insert includes a bore which is aligned with the metering chamber in the first transverse position of the dispensing cylinder, and wherein both the insert and the dispensing chamber are rotatably received in the dispensing head for conjoint rotation between a first radial position in which the insert bore and metering chamber are in communication with the feed hole and a second radial position in which the insert itself blocks the feed hole to store the powdered drug in the storage means in an air-tight manner.

15. An inhaler for administering a powdered drug nasally, which comprises:
(I) storage means for containing a quantity of the powdered drug, wherein the storage means includes:
 (A) a feed hole through which the powdered drug may be removed from the storage means; and
 (B) means for removing moisture from the stored drug; and
(II) dispensing means operatively connected to the feed hold of the storage means for dispensing the powdered drug nasally, wherein the dispensing means comprises:
 (A) a nozzle shaped to be received in a nasal passage of the user, wherein the nozzle includes a dispensing passageway;
 (B) means for measuring and transferring a pre-determined charge of the powdered drug from the storage means to the nozzle means, wherein the pre-determined charge has a volume less than the stored quantity of the powdered drug originally contained in the storage means; said measuring and transferring means comprising:
 (i) a body portion adjacent the nozzle and having a transverse bore therein which operatively connects the dispensing passageway in the nozzle with the feed hole in the storage means, wherein the feed hole and the dispensing passageway are transversely offset relative to one another at the points where they enter the transverse bore; and
 (ii) a dispensing cylinder having a metering chamber which may be selectively aligned with either the feed hole or the dispensing passageway, wherein the dispensing cylinder is slidably received in the transverse bore for movement between a first transverse position in which the metering chamber is aligned with the feed hole and a second transverse position in which the metering chamber is aligned with the dispensing passageway; wherein the metering chamber in its first position can be filled with the pre-determined charge of the powdered drug when the inhaler is manipulated and in the second position places the pre-determined charge of the powdered drug into the dispensing passageway for inhalation by the user;
 (iii) vent means for allowing ambient air to be drawn into the nozzle means for carrying the powdered charge therein upwardly into the nasal passage of the user upon inhalation of the user; said vent means comprising an air vent located in the dispensing cylinder in communication with the metering chamber, wherein the air vent is located adjacent one end of the dispensing cylinder such that it is closed by the transverse bore in the first position of the dispensing cylinder and is located outside of the body portion of the dispensing head in the second position of the dispensing cylinder so that the inhaling air flow passes in through the air vent, through the metering chamber and into the dispensing passageway, whereby the vent means is operative only in the second position of the cylinder.

* * * * *

UNITED STATES PATENT AND TRADEMARK OFFICE
CERTIFICATE OF CORRECTION

PATENT NO. : 4,274,403
DATED : June 23, 1981
INVENTOR(S) : Roger L. Struve

It is certified that error appears in the above-identified patent and that said Letters Patent are hereby corrected as shown below:

Column 2, Line 68 change "dispending" to --dispensing--.

Column 8, Line 32 change "passageway.passageway." to --passageway.--

Signed and Sealed this

Sixth Day of October 1981

[SEAL]

Attest:

GERALD J. MOSSINGHOFF

Attesting Officer           Commissioner of Patents and Trademarks